United States Patent [19]

Preti et al.

[11] 4,119,089
[45] Oct. 10, 1978

[54] METHOD OF PREDICTING AND DETERMINING OVULATION BY MONITORING THE CONCENTRATION OF VOLATILE SULFUR-CONTAINING COMPOUNDS PRESENT IN MOUTH AIR

[75] Inventors: George Preti, Philadelphia; George R. Huggins, Wallingford, both of Pa.; Joseph Tonzetich, Vancouver, Canada

[73] Assignee: Trustees of the University of Pennsylvania, Philadelphia, Pa.

[21] Appl. No.: 764,750

[22] Filed: Feb. 2, 1977

[51] Int. Cl.² ............................................. A61B 10/00
[52] U.S. Cl. .................................... 128/2 R; 23/230 B
[58] Field of Search ..................... 128/2 W, 2 R, 1 C; 23/230 B, 253 TP, 232 C

[56] References Cited

U.S. PATENT DOCUMENTS 3,472,738  10/1969  Foster ................................. 23/230 B
3,507,269  4/1970  Berry ................................. 23/253 TP

OTHER PUBLICATIONS

Tonzetich, J. et al., "Production of Volatile Sulphur Compounds from Cysteine, Cystine and Methionine by Human Dental Plaque", Arch. Oral Biology, 1971, v. 16, pp. 599–560.

Tonzetich, J. "Direct Gas Chromatographic Analysis of Sulphur Cmpds. in Mouth air in Man", Arch. Oral Biology, 1971, v. 16, pp. 587–597.

Lindhe, Jan et al., "Gingival Exudation During the Menstrual Cycle," Jrnl. of Periodontal Research 2: 194–198, 1967.

Prout, R. E. et al., "A Relationship Between Human Oral Bacteria and the Menstrual Cycle", Jrnl. Periodontal Rec. 41: 98–101 (1970).

Hopps, R. M., "Flow of Gingival Exudate as Related to Menstruation & Pregnancy," Jrnl. Periodontal Research 2: 13–20 (1967).

Primary Examiner—Robert W. Michell
Assistant Examiner—Francis J. Jaworski
Attorney, Agent, or Firm—Benasutti Associates, Ltd.

[57] ABSTRACT

A novel method is provided for precisely predicting and then ascertaining the time of ovulation by monitoring the mouth air of a female, a first peak after menses in the concentration of said volatile sulfur-containing compounds in said mouth air predicting ovulation by about 5 to 7 days, and a second increase thereafter being indicative of ovulation. Alternatively, a method is provided wherein TPTZ is utilized to sense secondary characteristics associated with the production of volatile sulfur compounds for the purpose of providing a simple colorimetric home test for determining the precise time of ovulation.

27 Claims, 6 Drawing Figures

METHOD OF PREDICTING AND DETERMINING OVULATION BY MONITORING THE CONCENTRATION OF VOLATILE SULFUR-CONTAINING COMPOUNDS PRESENT IN MOUTH AIR

RELATED APPLICATIONS

The present application is related to U.S. patent application Ser. No. 519,220, filed Oct. 30, 1974, now U.S. Pat. No. 3,986,494, and U.S. Ser. No. 564,348, filed Apr. 2, 1975, now U.S. Pat. No. 4,010,738, each of which applications are assigned to the trustees of the University of Pennsylvania; these patent applications are hereby incorporated by reference as if fully set forth herein.

BACKGROUND OF THE INVENTION

The present invention relates to the field of detection and diagnosis of ovulation in female mammals through the detection of secondary characteristics occurring during or at the time of ovulation, and more particularly to the detection of ovulation by these secondary characteristics as they appear in human females.

There has for many years been a need to detect and diagnose the precise time of ovulation in a given female mammal. It can be of great importance, for example, to pinpoint the time of ovulation to insure that fertilization occurs and that offspring is produced. Alternatively, it may be important for other medical reasons to diagnose ovulation.

Economically, it is of great interest to livestock breeders, particularly cattle breeders, to be able to detect the times of ovulation of the cows in the herd in order to insure that offspring production is maximized. In dairy herds, for example, conventional techniques for determining ovulation result in as many as 50% of the ovulatory cycles of a given cow being undetected by the breeder. Since artificial insemination is now almost exclusively used to produce fertilization, auxiliary means capable of detecting each incidence of ovulation is in great demand.

Heretofore, there has been no simple, inexpensive test by which a doctor or other individual may diagnose the occurrence of ovulation. Since the occurrence of subsequent vaginal bleeding may not be a reliable indicator that ovulation has indeed occurred, and since in many instances it would be desirable to begin treatment for a suspected condition without awaiting the onset of menstruation to determine that ovulation has, in fact, occurred, a need exists for a method to accurately diagnose the occurrence of ovulation at the time of its occurrence during a menstrual cycle.

The occurrence of ovulation can be established with some certainty through various prior art methods. Even though the only irrefutable method of proving ovulation is the occurrence of conception (or occasionally the actual recovery of the egg), several testing techniques are available which may be used to presumptively confirm the occurrence of ovulation. At present, these tests can give a reasonably good indication that ovulation has or is just about to occur, however, each of these tests are subject to certain disadvantages which affect either the practicality or the reliability of these tests.

1. Surgical Techniques

Surgical techniques for detecting ovulation either call for incisions to be made which facilitate the observation of the corpus luteum of the ovary for physical signs of ovulation, or require that attempts be made to recover the ovum from the oviduct. These have not gained widespread acceptance as simple, safe or reliable techniques.

2. Clinical Techniques

Clinical evaluation has often been suggested as a method of detecting the time of ovulation. One such method focuses upon the appearance of pelvic discomfort at the time of expected ovulation. This "mittelschmerz" is thought to be brought about either by distention of the ovary or by peritoneal irritation from bleeding as a result of follicular rupture. Unfortunately, even among those patients who experience monthly "mittelschmerz", the symptom does not appear to be particularly related to the time of ovulation. Similarly, a mucoid vaginal discharge may sometimes be observed which is the result of increasing secretion from the cervix. This discharge may sometimes be noted immediately prior to ovulation and may be observed in conjunction with premenstrual mastalgia, slight edema or tension. While suggesting that ovulation is in fact occurring, the various techniques described above have proved of little value in precisely predicting or detecting the time of ovulation.

Perhaps the most popular and widely used method of detecting and timing ovulation is the graphic recording of the waking temperature at basal conditions. Using this method, an extremely dedicated woman with uniform daily habits can determine the time of ovulation within two days after its occurrence. In recording the basal body temperature, a rise in temperature is commonly associated with the beginning of the luteal phase, but can vary from the actual time of ovulation by as much as 72 hours. A theoretical basal body temperature chart is illustrated in FIG. 1 and actual basal body temperature charts are illustrated in FIGS. 5 and 6 in connection with the examples set forth herein. In view of the fact that a basal body temperature chart determines the time of ovulation within 2 days after its occurrence, this method is not a reliable one for diagnosing ovulation in that, in most if not all instances, ovulation will have passed before a determination of ovulation can be made.

3. Biochemical or Histological Techniques

In more recent years, various biochemical and histological methods have been developed for detection of the approximate time of ovulation. These methods include histological evaluation of epithelial and/or endometrial samplings, the use of differential staining techniques on vaginal desquamate and the measurement of hormonal levels throughout the menstrual cycle.

It has long been known that a normal menstrual cycle is accompanied by certain cyclic variations in the concentrations of certain hormones appearing in the blood. In humans, the preovulatory rise in serum estrogens coupled with a sharp rise in luteinizing hormone (LH) levels as determined by radio-immunoassay of serially drawn blood samples, is perhaps the most accurate indicator of impending ovulation. Ovulation most likely occurs 12-24 hours after maximum LH levels. A subsequent rise and persistent high level of serum progesterone indicates that ovulation has occurred. Since these determinations are expensive and not widely available, other clinical parameters are used to predict the fertile period, and more particularly, ovulation. These rely on various physical, histological and biochemical changes which may be somewhat more easily monitored.

Taking the day of ovulation as day 0 (the point commonly referred to as being "midcycle"), estrogen levels normally begin to rise on approximately day −3. However, in some women, estrogens may be found to rise as early as day −6, or even earlier. This pre-midcycle estrogen rise is followed by a sharp rise in luteinizing hormone, which is generally accepted to trigger ovulation. Shortly after ovulation, on day +2 or day +3, the level of progesterone begins to rise and remains at sustained levels until day +8 or day +10. The theoretical level of estrogens and progesterone are illustrated in FIG. 1 and actual estrogen and LH (luteinizing hormone) levels for different cycles are shown in FIGS. 4, 5 and 6. Data for these hormones for several experimental subjects is reported in connection with the particular examples set forth hereinafter.

As discussed above, in humans, ovulation is preceded by a large rise in serum estrogens which, in turn, is thought to trigger the release of luteinizing hormone (LH) from the pituitary's anterior lobe. This results in a sharp rise in serum levels of this gonadotropin. Ovulation most likely occurs 12–24 hours after maximum LH levels. It has been demonstrated that fluctuations in the concentrations of gonadotropins and steroid sex hormones during the menstrual cycle correlate with periods of marked changes in cytology and secretory activity in the epithelial lining of the genital tract and oral mucosa of young females.

Certain biochemical tests have also been developed for the purpose of pinpointing the time of ovulation. One such test, referred to as the cervical mucous test, has been devised for the purpose of predicting the time of ovulation through the measurement of the concentration of glucose present in the cervical mucus.

Another test is the monitoring of salivary alkaline phosphatase levels which generally appear to parallel plasma estradiol (estrogen) levels. Unfortunately, the presence of alkaline phosphatase shows significant daily variations, not only between individuals but also within any given individual. Furthermore, this alkaline phosphatase test tends to provide its characteristic indication during a period ranging from 1 to 10 days prior to the actual occurrence of ovulation. Due to this uncertainty, this test appears to be unreliable in predicting either the onset of the fertile period or the actual occurrence of ovulation.

Even more recently, in U.S. patent application Ser. No. 519,220, filed Oct. 30, 1974, and Ser. No. 564,348, filed Apr. 2, 1975, various methods are described whereby vaginal secretions are monitored for certain cyclical changes in volatile organic compounds, particularly lactic acid, acetic acid and urea, for the purpose of predicting and/or detecting the time of ovulation. While these methods are reliable and have met with some success, the fact that they are directed to and require the sampling of vaginal secretions may reduce the probability that these methods will quickly gain widespread acceptance in human populations. Theoretical levels of lactic and acetic acid are illustrated in FIG. 1 and actual levels of lactic acid and urea are illustrated in FIGS. 5 and 6.

It may therefore be concluded that while there are many clinical, histological and biochemical methods which are appropriate for use in detecting the time of ovulation, there is still a substantial need for simple, universally acceptable methods for detecting and diagnosing the precise time of ovulation.

4. Prediction of the Fertile Period

It is generally accepted that the maximum survival function of spermatozoa capable of fertilizing an ovum is approximately 3 days following coitus. Although theoretically any coitus prior to ovulation entails a certain risk of pregnancy, as a practical matter, abstinence from sexual intercourse for the three days prior to ovulation is generally considered to be a "safe" period prior to the occurrence of ovulation. It is generally recognized that the ovum is susceptible to fertilization for a matter of hours. In the rabbit or rat, for example, there is a decreased fertility after the 6th hour. It is generally recognized that the human ovum is fertilizable probably for about 12 hours and certainly for no more than 1 day. The human fertile period, then, is made up of no more than 4 days out of the entire menstrual cycle. If it were possible to accurately predict this fertile period, it would theoretically be necessary to either abstain from intercourse or use alternate birth control methods only for that 4 day "fertile period" rather than for the entire menstrual cycle. Heretofore, the only widely used technique for predicting the fertile period of a female has been the method which relies upon basal body temperature determination of ovulation in a plurality of preceding cycles to determine the expected time of ovulation for future cycles. This method is not really directed to ascertaining the precise fertile period for a given cycle, but rather is intended to establish a statistically "dangerous" period during which coitus is likely to produce pregnancy. Since this information is based upon past performance, and since the time of ovulation varies markedly between different individuals as well as between cycles of a given individual, the period for abstinence must be long enough to considerably reduce the possibility of pregnancy.

One method for calculating the period for abstinence which has been suggested is that intercourse be avoided beginning at the time of menses and continuing until a sustained rise in basal body temperature has been observed. Alternatively, a patient may record 12 previous consecutive cycles, noting the longest and shortest cycles experienced during this interval. Since it is generally agreed that menses usually occurs about 14 days after ovulation, it has been suggested that the fertile period in a given cycle is between 18 and 11 days before menstruation. Using this period as the fertile period, the period for abstinence may be calculated by subtracting 11 days from the longest recorded cycle to arrive at the last unsafe day. Since an extremely regular woman would usually have a cycle which varies in length between 20 and 30 days, the shortest period of abstinence would be expected to range from day 8 to day 19, or more than one-third of the total cycle. It has been estimated that only 55% of the naturally occurring menstrual cycles are within the range of 25 to 31 days, and that even the most regular of women may have cycles which vary from 21 to 33 days. Consequently, it may be concluded that the irregularity and extreme length of the required period of abstinence makes the rhythm method based on basal body temperature and statistical prediction unacceptable to all but the most regular and dedicated of women.

Of the various techniques for detecting ovulation which have been considered above, none of these techniques have the practical capability of predicting the onset of ovulation sufficiently in advance to allow the prospective calculation of the period of abstinence. While certain of these tests may occasionally predict ovulation up to 10 days in advance of its occurrence, all of these tests are equally as likely to give no indication of ovulation until after the onset of the fertile period. This irregularity further precludes any possibility that the tests which do predict ovulation in advance could be used to shorten the period of abstinence since their irregularity would result in periods of abstinence which show no better statistical significance than those based upon the natural occurrence of menstruation. The relative failure of the various techniques discussed above to predict the fertile period in advance has led one commentator to conclude:

"The possibility of predicting ovulation by 3–4 days, and thus providing a couple with a period of abstinence no greater than 5 days is intriguing. John Rock, for one, views this approach with some optimism. Should such a method finally be worked out, it would be but another addition, albeit a vital one, to our armamentarium for controlling the population growth of the world. Certainly, in many nations and even among many couples in our own country, much education would be required to convince the male that he should abstain, even for so short an interval as 5 days, and much effort would have to be expended before some males could look upon this as anything but an infringement of their rights as husbands and lovers. It is clear, nevertheless, that if we could find a way to predict ovulation, we would provide a very natural means of family spacing—in fact, the most physiologic means imaginable. Even if it should require somewhat greater effort than the other methods now available, it would be a real boon to many people, regardless of their religious affiliation. It should be kept in mind that even taking a pill once a day requires some effort and intelligence, and certainly the mechanical contrivances now available are, to say the least, inconvenient." ("The Present Status of Rhythm Techniques", Luigi Mastroianni, Jr., M.D., Clinical Obstetrics and Gynecology, Volume 7, No. 3, 1964, pages 874–875).

SUMMARY OF THE INVENTION

Generally, the present invention is predicated upon the finding that certain volatile sulfur-containing constituents of mouth air exhibit a unique cyclical behavior during the course of a female's menstrual cycle, and accordingly, provides a novel method for predicting and diagnosing ovulation by monitoring the concentration of certain volatile sulfur-containing compounds during that cycle beginning after menses, and by providing indicator means for quantitatively and qualitatively responding to said volatile sulfur-containing compound(s), whereby significant increases in the concentration of said compound(s) first predict the onset of the fertile period and then are indicative of ovulation.

Generally, the method of the present invention comprises the steps of monitoring mouth air for the concentration of certain volatile sulfur compounds, by providing an indicator means for qualitatively and quantitatively responding to the concentration of said volatile sulfur compounds in mouth air, whereby the means for indicating that concentration predicts by approximately 5 to 7 days the occurrence of ovulation, and/or diagnoses the precise time of ovulation. Accordingly, the method of the present invention is believed to be useful in accurately predicting and diagnosing the fertile period of a given female, and is therefore useful as a birth control method in that current "rhythm" techniques of birth control requiring long periods of abstention from coitus may be replaced with a relatively shorter period of abstention which is substantially co-extensive with a 4 to 5 day fertile period.

The present invention therefore provides a simple, reliable method of predicting the onset of the fertile period or ovulation and/or of detecting ovulation by monitoring the volatile sulfur content of mouth air, which content has been found to "peak" or "spike" approximately 5 to 7 days prior to ovulation and again at the time of ovulation. The volatile sulfur content of mouth air is believed to be a secondary characteristic which is responsive to elevated levels of female sex hormones. The rationale for relying upon the monitoring of volatile sulfur content of mouth air as a reliable ovulation indicator is supported by the correlation between the data collected and other known manifestations such as the increased metabolic activity of saliva of individuals exhibiting periodontal involvement. For example, saliva samples from diseased mouths putrefy more rapidly than those from essentially normal mouths. The increased rate of salivary putrefaction, a process involving degradation of proteinaceous substrates by the oral microflora, results in intensification of malodour of saliva and mouth air. The principal malodorous components are identifiable as hydrogen sulfide and methyl mercaptan, which arise through bacterial decomposition of sulfur-containing proteins associated primarily with exfoliated epithelial cells. It is postulated that the method of the present invention detects secondary characteristics of ovulation which may in some way be correlated to or at least appear at similar times with apparent symptoms of gingival inflammation at ovulation, increases in numbers of desquamated epithelial cells at ovulation and periodontitis, and the increase in total bacterial counts at ovulation. It is further postulated that these conditions could possibly suggest that the prevailing conditions in the oral cavity are at least favorable for accelerated production of volatile sulfur compounds during both these times in the menstrual cycle, although the relationship between these conditions and the sharp concentration changes in volatile sulfur compound concentrations is not fully understood at this time.

For example, elevated levels of female sex hormones appear to lower the threshold sensitivity of the periodontal tissue to inflammation with the severity of tissue involvement believed to be reflected by the magnitude of increase in the volume of gingival exudate. Correspondingly, the amount of gingival fluid is greatest near ovulation and least at menstruation. Greatest fluctuations in the volume, due to hormonal influences, are found in cases with pre-existing chronic gingivitis. This increased flow of gingival exudate is attributed to the impairment of microcirculation, characterized by increased vascularity and permeability of venules and capillaries of the affected gingival tissue. Similar degenerative changes are elicited by bacterial plaque, a recognized primary factor in etiology of periodontal disease. Nonetheless, it is not understood how, in this relatively complex microbiological environment, volatile sulfur-containing compounds are caused to be produced in the particular concentrations as described hereinafter.

Alternatively, another embodiment of the present invention contemplates use of TPTZ which is believed to act as an indicator which is correlated to the rate of production of volatile sulfur compound(s) in saliva, said alternate embodiment providing the advantages of a simple, home, colorimetric test which may replace or supplement the mouth air indicator means of the preferred embodiment for the purpose of simplifying the indicator means required for use in the present inventive method.

Accordingly, the primary object of the present invention is to provide a simple, safe, reliable method of predicting and/or diagnosing ovulation by monitoring the concentration of certain volatile sulfur compounds in mouth air over the course of a given menstrual cycle; a first marked increase in the concentration of volatile sulfur compounds after menses being predictive of ovulation and a second marked increase in said concentration being diagnostic of ovulation.

Another object of the present invention is the provision of a simple colorimetric test which similarly provides for the prediction and diagnosis of ovulation.

A further object of the present invention is the elimination of any need to conduct extensive histological or biochemical tests to predict or determine the occurrence of ovulation.

These and other objects of the present invention will become apparent from the following more detailed description.

DETAILED DESCRIPTION OF THE PREFERRED EMBODIMENTS AND EXAMPLES

Figure 1:
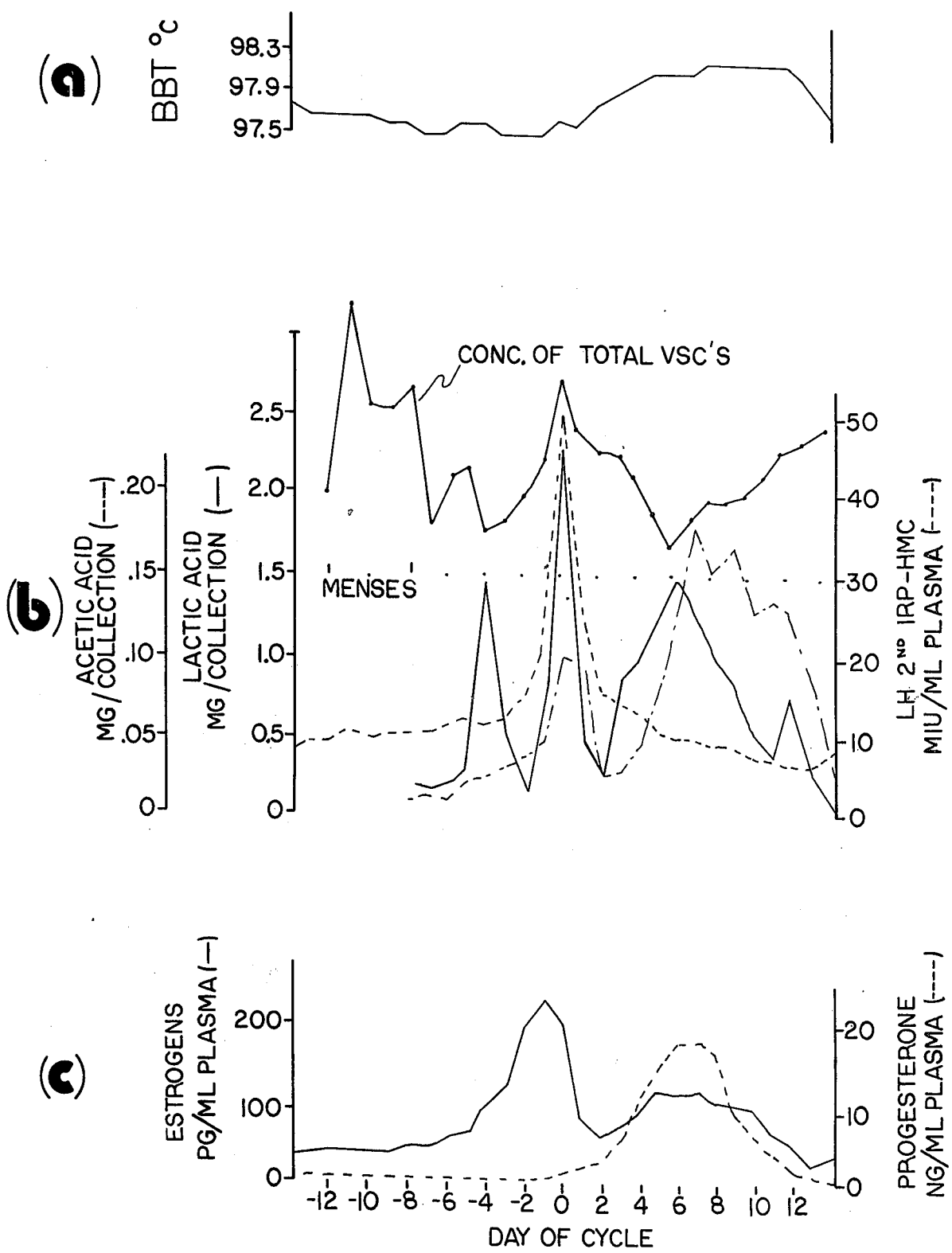
FIG. 1 is a graph for one menstrual cycle of the theoretical levels of plasma estrogens, progesterone and LH; vaginal secretion acetic and lactic acid data and basal body temperatuure values and over which theoretical values for the total volatile sulfur compound content of mouth air have been superimposed in the same scale as illustrated in FIG. 2.

As used herein, the term volatile sulfur compounds (VSC) shall preferably refer to the following compounds:

$(CH_3)_2S$ $CH_3SH$ $H_2S$

Five healthy female subjects, between the ages of 22 and 30, volunteered for the study. Complete medical histories and physical examinations indicated that all five subjects had a history of normal regular menses and exhibited no evidence of systemic, oral or pelvic pathology. None of the subjects were taking oral contraceptives. Subjects were instructed to maintain a basal body temperature chart and on mornings prior to mouth air analysis, were asked to abstain from exercising oral hygiene, smoking, and ingestion of food and liquid.

The study represents findings of 12 ovulatory menstrual cycles compiled from evaluations of mouth air from individual subjects during two or three consecutive cycles. In three cycles, one from each of three subjects, ovulation was documented by hormonal profiles which included plasma estrogens, progesterone, and LH. These assays were performed using previously documented techniques. In the remaining cycles, ovulation was assumed from the BBT chart and the onset of the next menses. Incidents of sexual arousal or coitus, the intake of foods high in sulfur content, as well as periods of physical discomfort or stress were also recorded on the BBT chart.

The levels of hydrogen sulfide ($H_2S$), methyl mercaptan ($CH_3SH$) and dimethylsulfide ($(CH_3)_2S$) in mouth air were performed by gas chromatography (GC). Duplicate analyses were performed each day these levels were measured. Analyses were begun at tne onset of menses and continued each day through the fourth day of the hyperthermic phase as determined from a subject's BBT chart. Thereafter, VSC's were measured on alternate days until the start of the next menses. All determinations were carried out between 7 a.m. and 9:30 a.m., with each individual being evaluated at the same time each morning.

For analysis, aliquots of mouth air were aspired from the mouth directly into a 10 ml sample loop component of a pre-column, air-actuated, automatic injection system. Then the contents in the loop were transferred via a 10-port valve onto a 24 ft. × ⅛ in. O.D. fluorinated ethylene propylene (FEP) Teflon column packed with 5% polyphenyl ether and 0.05% phosphoric acid on 40–60 mesh Chrom T and chromatographed isothermally at 70° C. The employed standardized pressures and flow rates of high purity carrier and burner gases were: carrier, ultra zero air (55 psig) — 20 ml/min; burner gases, $H_2$(40 psig) — 80 ml/min, and ultra zero air (55 psig) — 60 ml/min. The sulfur-containing fractions were detected with a Tracor MT-550 gas chromatograph equipped with a flame-photometric detector and accessories (Micro Tek Instruments Corporation, Austin, Tex.) adapted for selective detection and quantitation of subnanogram (ng) levels of sulfur-containing compounds. The optical emissions from decomposition of $H_2S$, $CH_3SH$, and $(CH_3)_2S$ were displayed as individual peaks on a 1-mV Tracor MT-11 recorder and amounts calculated as peak areas using a 3307-B Hewlett-Packard digital integrator (Hewlett-Packard, Avondale, Pa.). The entire procedure for one analysis took 10 minutes to complete.

The concentrations of the three sulfur components were calculated from standard graphs derived from analyses of known concentrations of compounds. Individual standard peak area curves were prepared from all three compounds by diluting the corresponding permeation tube standards (Analytical Instrument Development Inc., West Chester, Pa.) to desired concentrations with $N_2$. The results are expressed in nanograms of $H_2S$, $CH_3SH$, $(CH_3)_2S$ in 10 ml of mouth air.

During seven of the 12 cycles, the small organic molecules found in the subject's vaginal secretions were monitored concomitantly with the volatile sulfur compounds (VSC) of mouth air. Secretions were collected via commercially available vaginal tampons using a previously documented schedule and analysis technique. See U.S. patent application Ser. No. 519,220, filed Oct. 30, 1974, and Ser. No. 564,348 filed Apr. 2, 1975. The latter employs both GC and gas chromatography — mass spectrometry (GC-MS) to elucidate the type and amount of organics present regardless of structural type.

All of the VSC monitored underwent cyclic variation. In 10 of 12 cycles studied, these compounds increased 2–5 fold in concentration within ±48 hours of the day of ovulation. Variations were found in the levels of VSC across subjects; however, levels for each subject were fairly consistent from one cycle to the next. Concentrations of $[(CH_3)_2S]$ never exceeded 2 ng/10 ml mouth air, while maximum levels of the other two compounds reached 4 to 8 ng/10 ml air. The two cycles shown in FIG. 1 are representative of the variations seen in the levels of the VSC and the cyclicity displayed by them.

Day −9 for subject M is the first day following cessation of menses while days −16 through −10 for subject E encompass the days of menstruation and 2 days following it. In both cycles, these days are characterized by high and/or increasing levels of ($H_2S$) and ($CH_3SH$). In all cycles, 71% displayed higher levels of these compounds during and for 1–3 days following menses than during their mid-proliferative phase.

Subject M (FIG. 3) shows a sharp increase in both $H_2S$ and $CH_3SH$ on day −6. This increase, occurring during the mod-proliferative phase, was seen during 84% of the cycles. Cycle I from subject E does not display such a rise at this time. Of interest was the fact that in the 3 cycles where hormonal profiles were obtained, this increase occurred concomitant with start of the rise in plasma estrogens, as will be shown below.

Figure 2:
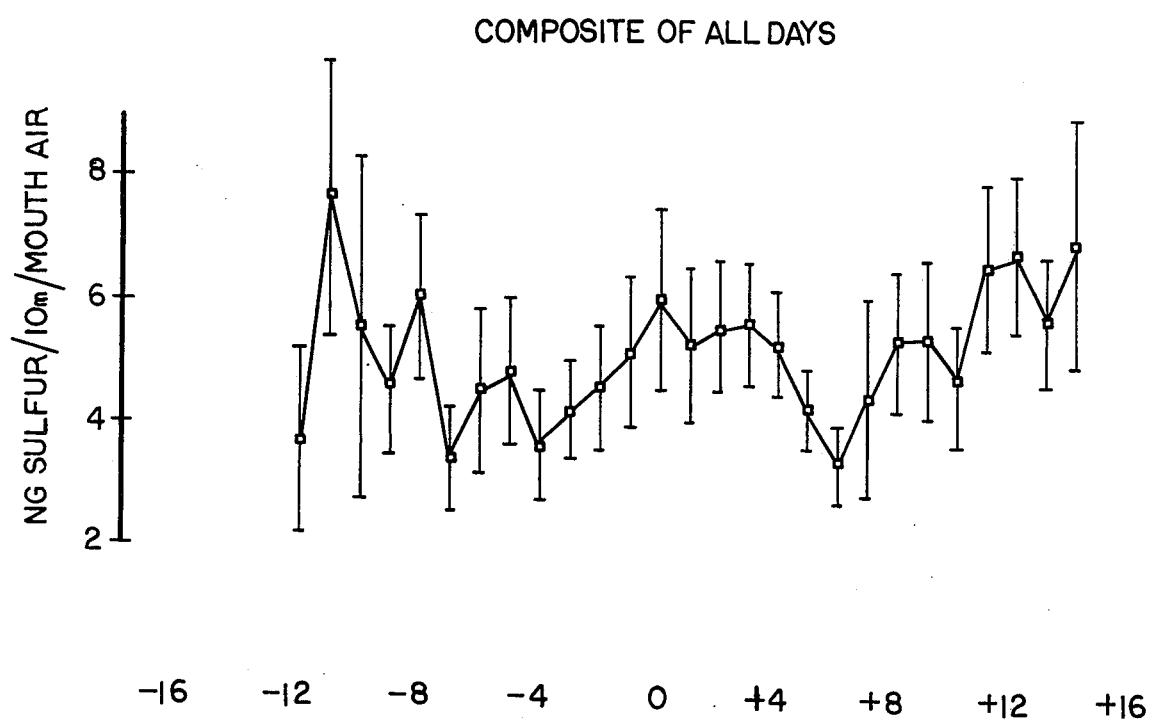
FIG. 2 is a graph of the concentrations of volatile sulfur compounds over one menstrual cycle which is based upon composite data collected and analyzed for a plurality of experimental subjects.
Figure 3:
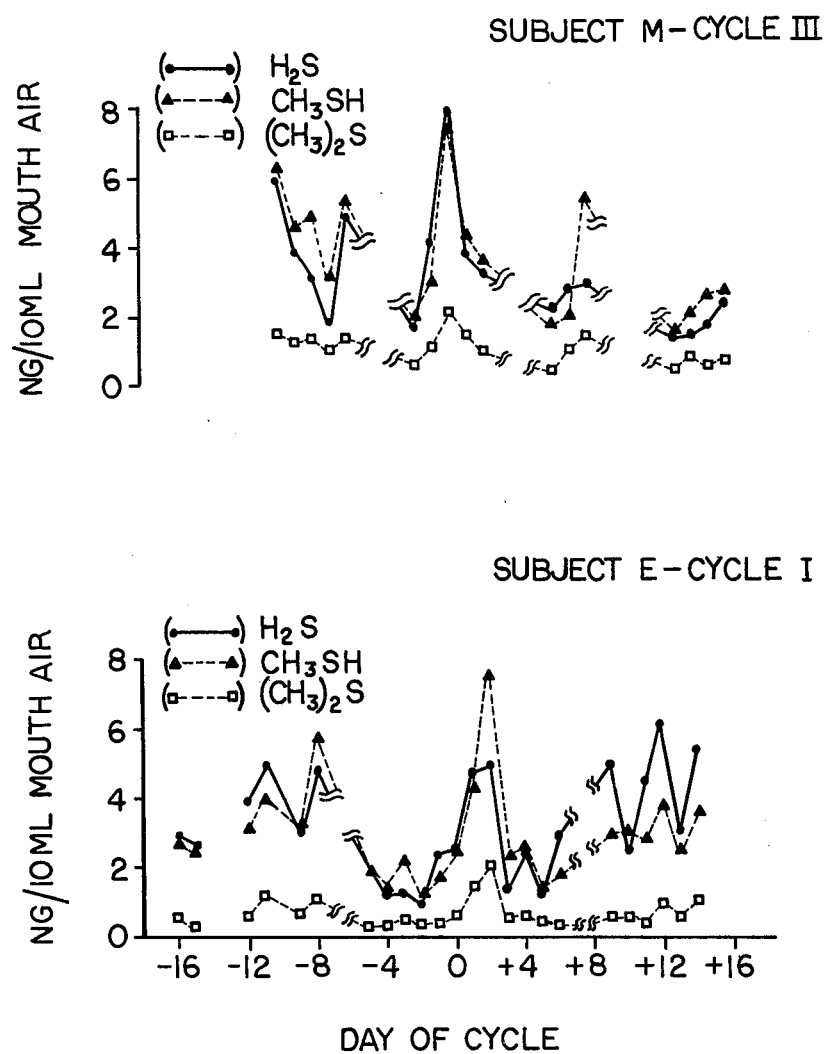
FIG. 3 is a graph illustrating changes in concentration of volatile sulfur compounds (VSC) of mouth air throughout one cycle, each from subjects M and E; the shaded areas on the abscissa indicating the days of menstrual bleeding, mouth air samples being obtained daily around midcycle. Both subjects exhibit a single, sharp increase in all three VSC within 48 hours of the day of ovulation. Subject M's profiles also illustrate distinct increases during the proliferative phase on day $-6$, mid-luteal phase on day $+8$, and as the next menses draws closer.

The sharp midcycle rise in VSC is clearly illustrated in FIG. 3. In the 3 cycles where documented hormonal profiles were obtained, the midcycle rise closely corresponded to the LH surge as may be seen in Table 2. Total nanograms of sulfur, $(CH_3)_2S$ and LH are plotted throughout two representative cycles in this cycle. Since $H_2S$ and $CH_3SH$ are present in greater quantities then $(CH_3)_2S$, when total nanograms of sulfur are plotted separately with $(CH_3)_2S$, separate maxima are seen for both plots at midcycle. The midcycle maximum of $(CH_3)_2S$ coincides with the LH surge for both cycles shown in FIG. 2. Dimethylsulfide reached a separate midcycle maximum in 33% of the cycles.

During the luteal phases of all cycles, increases in VSC were seen both during the mid-luteal (50%) and ore-menstrual part of the cycle (84%). All of the cycles illustrated here (Tables 1 and 2) show a gradual or sharp increase in VSC concentration as the onset of the next menses draws closer.

Figure 4:
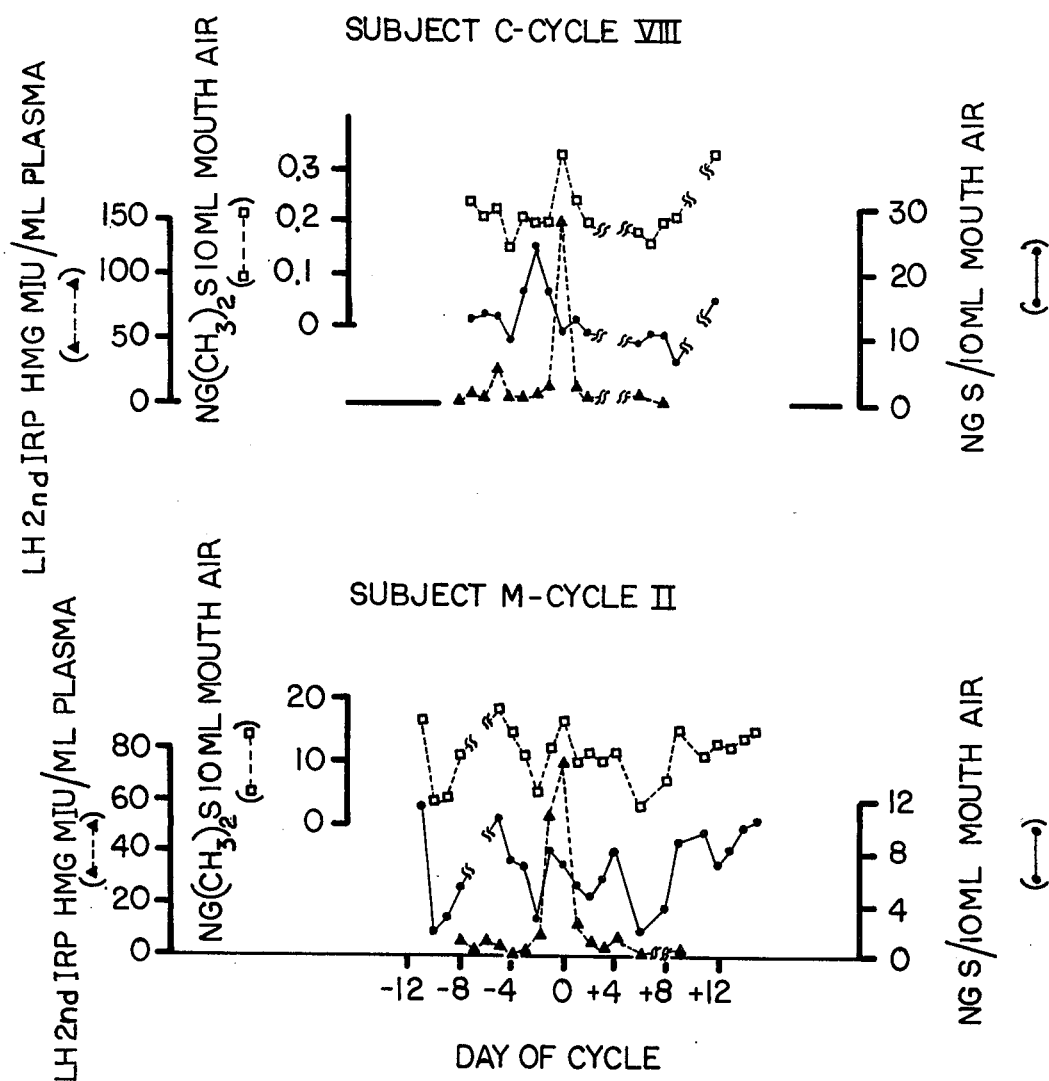
FIG. 4 is a graph illustrating changes in concentration of LH, total sulfur and $(CH_3)_2S$ throughout one representative cycle from subjects C and M; shaded areas being indicative of the days of menstrual bleeding. The levels (ng) of both the total S and $(CH_3)_2S$ are elevated in the proliferative phase of both subjects. The midcycle increase in total S is less sharp for subject M than C. Both total S and $(CH_3)_2S$ increase gradually as the next menses draws closer.

As noted above, in 7 of the cycles, cyclical changes in small organic molecules found in subject's vaginal secretions were also monitored. From previous studies, lactic acid and urea have been shown to increase sharply during the proliferative phase and midcycle; in addition, other increases in these compounds are found during the luteal phase. In Tables 3 and 4, cyclical changes in lactic acid, urea and total nanograms of sulfur are plotted during 2 cycles. These are the same cycles shown in FIG. 4.

Subject C shows a marked increase in total S on day −2, coinciding with a large midcycle rise in lactic acid concentration. Urea undergoes only a small increase on this day. Subject M does not show as marked a rise in total S at midcycle, but a distinct jump is seen going from day −2 to −1. An increase in both lactic acid and urea is found on day +1.

Figure 5:
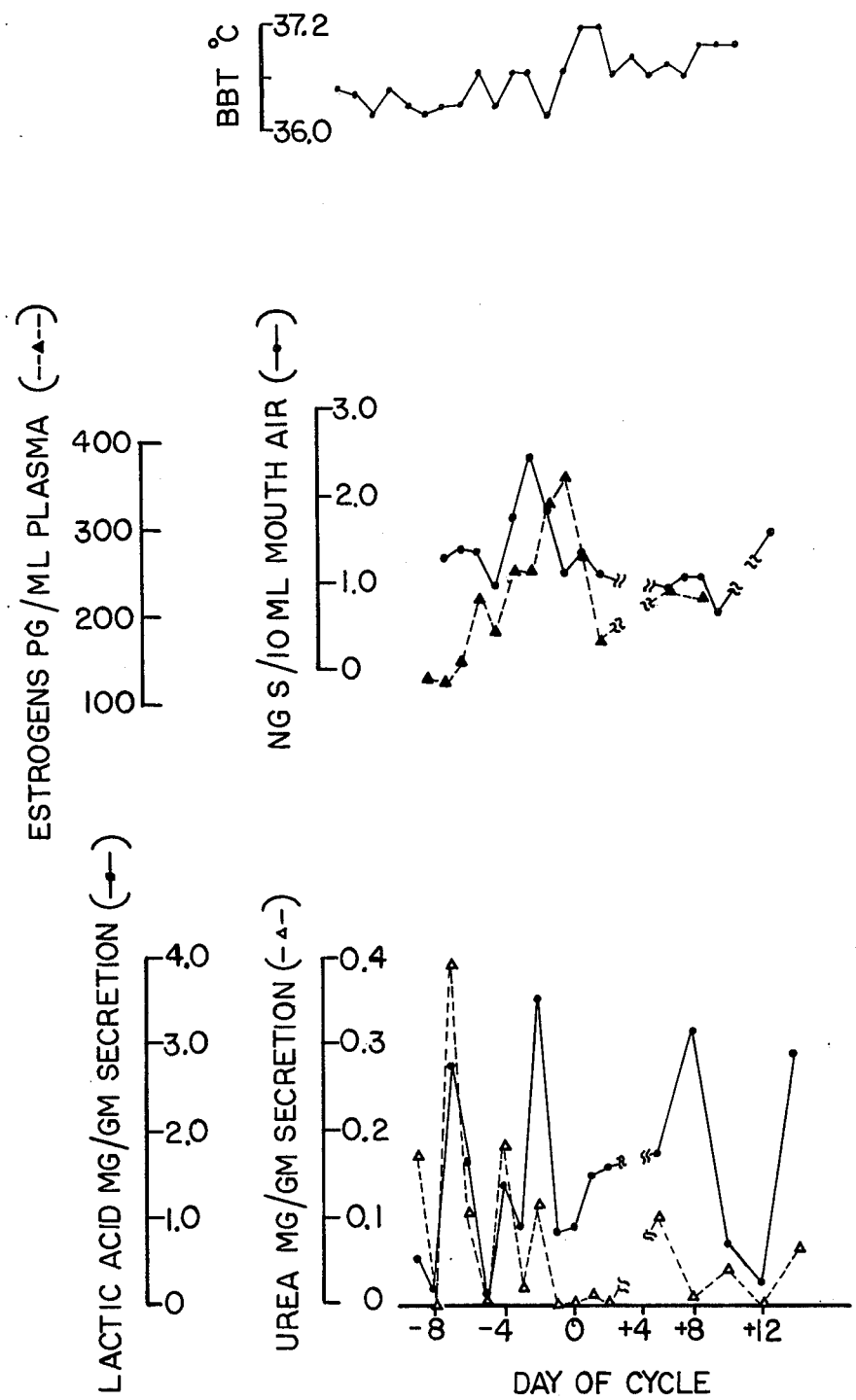
FIG. 5 is a graph illustrating changes in total ng of sulfur, estrogens, BBT, lactic acid and urea throughout one cycle from subject C. A proliferative phase rise in the concentration of both urea and lactic acid is illustrated which occurs on day $-7$, just before the onset of the preovulatory increase in plasma estrogens. The other increases in urea are evident, but of smaller magnitude. The total S of mouth air is only slightly elevated on days $-7$ to $-5$, the midcycle rise in lactic acid occurring on day $-2$, while the increase in total S occurs on day $-3$. A mid-luteal increase in lactic acid's concentration being seen on day $+7$, corresponding to a period of high progesterone levels. Elevated levels of lactic acid and total S are also seen on day $+13$, just before the onset of menstruation.
Figure 6:
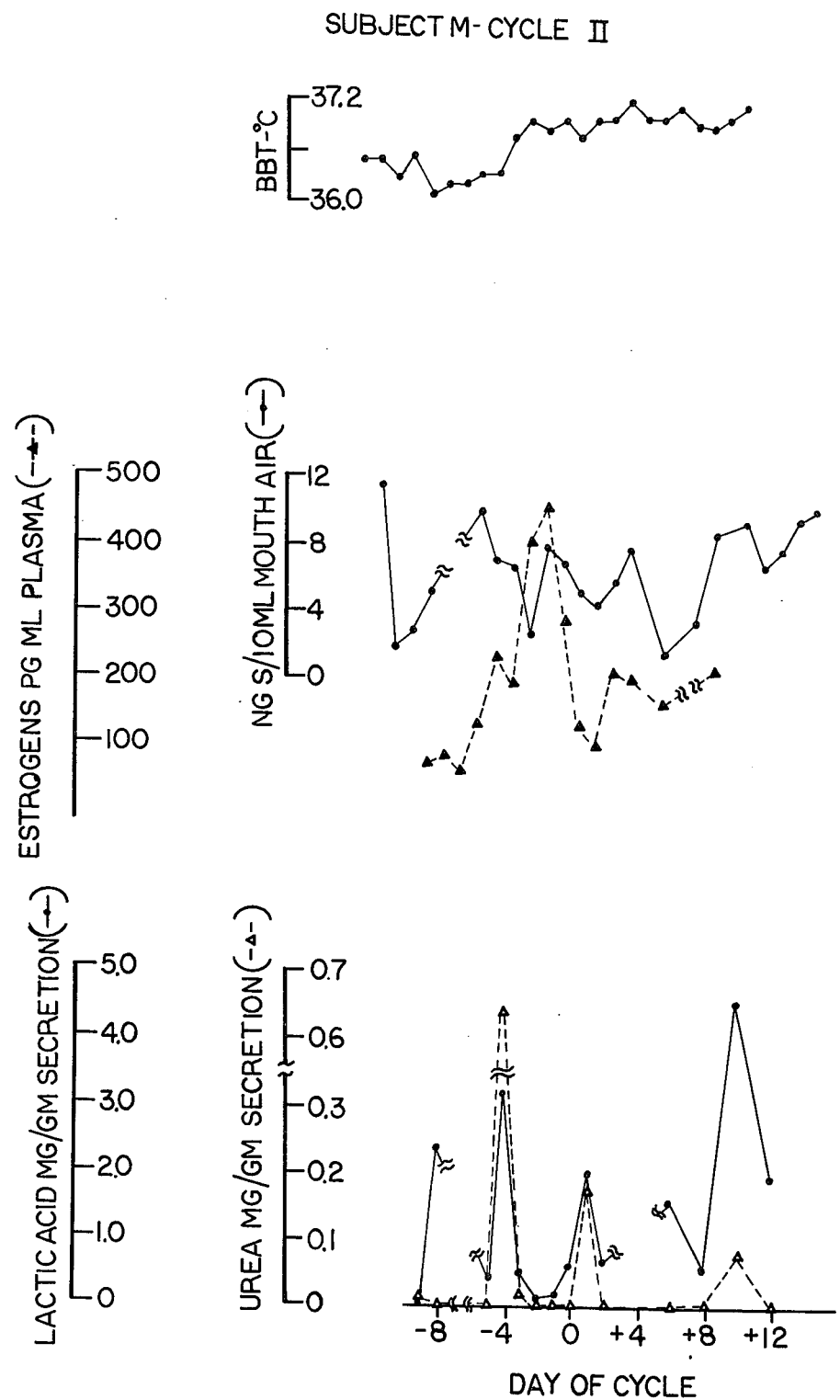
FIG. 6 is a graph illustrating changes in total S, estrogens, BBT, lactic acid and urea throughout a cycle from subject M. Two increases in the concentration of lactic acid are seen in the proliferative phases on days $-8$ and $-4$. The latter rise is concomitant with a large increase in urea concentration and closely coincides with the preovulatory increase in blood estrogens. Total S undergoes a large proliferative phase increase on day $-5$. Coincidental increases of both lactic acid and urea concentrations also occur at midcycle (day $+1$), while elevated levels of S are seen on day $-1$. No large increase in lactic acid was observed during the earlier mid-luteal phase, however, the increase in total S on day $+4$ coincides with the luteal phase estrogen maximum and increasing progesterone levels (not shown). Late luteal phase increases are seen for urea and lactic acid on day $+10$. Total S increases to its highest levels as the next menstrual cycle approaches.

The proliferative phase increase in mouth air sulfur, referred to above, may be seen in FIGS. 5 and 6. In both cycles, this rise in $H_2S$ and $CH_3SH$ occurs within 24 hours of the rise in urea and lactic acid at this time. It should be noted that urea and lactic acid also increase in the late luteal phase as does sulfur in the mouth air of these subjects.

Alternatively, the present invention contemplates the use of several different indicator means: TPTZ (2,3,5-triphenyltetrazolium chloride) is one such indicator producing a colorimetric indication of the rate of VSC production. TPTZ, a well-known hydrogen acceptor and indicator, is proportionally reduced according to the rate of conversion of disulfide linkage of cystine to cysteine (thiols), which reduction to triphenylformazan produces a red color change, which color change may be measured spectrophotometrically or by comparison to known standards. The methodology which may be employed in the use of TPTZ in accordance with this embodiment of the present invention is described in "Odour Production by Human Salivary Fractions and Plaque" by J. Tonzetich and R. C. Kestenbaum appearing in *Archives of Oral Biology*, Vol. 14, pp. 815–827 (1969) (Pergamon); see also "The Application of Instrumental Technique for the Evaluation of Odoriferous Volatiles from Saliva and Breath" by Richter and Tonzetich, Vol. 9, pp. 47-53, appearing in *Archives of Oral Biology*, each of which publications are incorporated herein by reference as if fully set forth herein. Another alternate indicator, believed most suitable for livestock use, is the use of trained animals, such as dogs, which are capable of distinguishing the volatile sulfur compounds to be detected. Accordingly, in practicing this embodiment, either the TPTZ or the animal method may be used in place of or in addition to other indicator means for quantitatively or qualitatively providing a colorimetric indication which is directly correlated to the rate of VSC production, a first significant peak in said rate following menses predicting ovulation by 5 to 7 days and a second peak indicating the occurrence of ovulation.

As used herein, it is to be understood that a significant "rise", "peak", or "spike" is one in which the concentration or rate increase over a period of ±48 hours is from at least about 1.5, and preferably from 2 to about 5 times as great as those pre-ovulatory levels.

It will be understood that various changes in the details, materials and arrangement of parts which have been herein described and illustrated in order to explain the nature of this invention may be made by those skilled in the art within the principle and scope of the invention as expressed in the following claims.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. A method of diagnosing ovulation in female mammals comprising the steps of:
   (a) monitoring the mouth air of one of said mammals during the fertility cycle for at least one volatile sulfur compound commonly occurring in said mouth air of said mammals; and
   (b) providing an indicator means for qualitatively and quantitatively responding to variations in the concentration of said volatile sulfur compound in said mouth air; whereby said means for indicating said variations in concentration diagnoses ovulation in said female mammal.

2. The invention of claim 1 wherein said female mammal is a human female.

3. The method of claim 2 wherein said volatile sulfur compound is a compound selected from the group consisting essentially of $H_2S$, $CH_3SH$, $(CH_3)_2S$ and mixtures thereof.

4. The invention of claim 1 wherein said female mammal is a cow.

5. The invention of claim 1 wherein said female mammal is a mare.

6. A method of diagnosing ovulation in a given female mammal comprising the steps of:
   (a) monitoring the mouth air of said mammal during the fertility cycle for at least one volatile sulfur compound commonly found in said mouth air;
   (b) providing indicator means for qualitatively and quantitatively responding to variations in the concentration of said compound in said mouth air; and
   (c) evaluating the correspondence of variations in concentration of said compound to the time of ovulation as indicated by other known ovulating indicators; whereby said evaluation establishes the quantitative and qualitative response which is diagnostic of ovulation in said given mammal.

7. The invention of claim 6 wherein said female mammal is a human female.

8. The invention of claim 6 wherein said volatile sulfur compounds are compounds selected from the group consisting essentially of $H_2S$, $CH_3SH$, $(CH_3)_2S$ and mixtures thereof.

9. The invention of claim 6 wherein said indicator means is a gas-chromatograph.

10. The invention of claim 6 wherein a second significant increase after menses in the concentration of said volatile sulfur compounds is diagnostic of ovulation.

11. The invention of claim 1 wherein said indicator means comprises means for detecting the concentration of volatile sulfur compounds which means responds to variations in said concentrations with a color change reaction which varies in intensity proportionally to the concentration of said volatile sulfur compounds.

12. A method of diagnosing ovulation in female mammals comprising the steps of:
    (a) monitoring the saliva of one of said mammals during the fertility cycle for at least one volatile sulfur compound commonly occuring in said saliva of said mammals; and
    (b) providing an indicator means for qualitatively and quantitatively responding to variations in the rate of said volatile sulfur compound production in said saliva; whereby said means for indicating said variations in concentration diagnoses ovulating in said female mammal.

13. The invention of claim 12 wherein said female mammal is a human female.

14. The invention of claim 12 wherein said volatile sulfur compound is a compound selected from the group consisting essentially of $H_2S$, $CH_3SH$, $(CH_3)_2S$ and mixtures thereof.

15. The invention of claim 12 wherein said indicator means is a means for detecting secondary characteristics associated with the rate of production of said volatile sulfur compound in said saliva.

16. The invention of claim 15 wherein said indicator means comprises means for detecting the rate of volatile sulfur compound production, which means responds to variations in said rate with a color change reaction which varies in intensity proportionally to the rate of said volatile sulfur compound production.

17. The invention of claim 16 wherein said means for detecting the rate of volatile sulfur compound production detects the rate of conversion of cystine residues to cysteines occurring in said saliva.

18. The invention of claim 17 wherein said means for detecting the rate of volatile sulfur compound production further comprises 2,3,5-triphenyltetrazolium chloride which is reduced to triphenyl-formazan to produce said color change reaction.

19. The invention of claim 18 wherein said color change is compared to colorimetric standards, said standards having been prepared by evaluating the correspondence of the rate of volatile sulfur compound production to the time of ovulation as indicated by other known ovulation indicators.

20. A method of diagnosing the onset of the fertile period and ovulation in female mammals comprising the steps of:

(a) monitoring the variation in concentration of the mouth air of one of said mammals during the fertility cycle for at least one volatile surfur compound commonly occurring in said mouth air of said mammals, significant increases in said concentrations corresponding to the 5th to 7th day prior to ovulation and the time of ovulation of said mammal; and (b) providing an indicator means for qualitatively and quantitatively responding to variations in the concentration of said volatile sulfur compounds in said mouth air; whereby responses of said means are predictive of the impending onset of the fertile period and ovulation in said female mammal.

21. A method of predicting the fertile period of female mammals comprising the steps of:

(a) monitoring the mouth air of one of said mammals for variations in concentration of at least one volatile sulfur compound commonly occurring in the mouth air of said mammals, beginning said monitoring at the cessation of menses; and (b) providing an indicator means for qualitatively and quantitatively responding to the variations in concentration of said volatile sulfur compound in said mouth air; whereby said means for indicating said variations in said concentration predicts the fertile period of said mammal.

22. The invention of claim 21 wherein said female mammals are human females.

23. The invention of claim 21 wherein a first response of said indicator means indicating an increase in said volatile sulfur compound concentration is predictive by 5 to 7 days of the time of ovulation of said female mammal, whereby the onset of the fertile period of said female is predicted by at least 2 days.

24. The invention of claim 23 wherein a second response of said indicator means indicating an increase in said volatile sulfur compound concentration and occurring at least 4 days after said first response indicates ovulation.

25. The invention of claim 24 wherein the volatile sulfur compound which is monitored in selected from either $H_2S$ or $CH_3SH$, and mixtures thereof.

26. A birth control method comprising the steps of:

(a) predicting the fertile period of a female mammal by monitoring the variation in concentration of the mouth air of said mammal for at least one volatile sulfur compound by beginning said monitoring at the cessation of menses, said variation preceding the onset of the fertile period of said mammal;

(b) providing an indicator means for qualitatively and quantitatively responding to variations in the concentration of said volatile sulfur compound in said mouth air, wherein a first response of said indicator means indicating an increase in said volatile sulfur compound concentration predicts the onset of the fertile period of said mammal by at least 2 days, and wherein a second response of said indicator means indicating an increase in said volatile sulfur compound concentration and occurring at least five days after said first response indicates ovulation; and (c) causing said mammal to avoid exposure to fertilization beginning no more than 2 days after said first increase and ending at least 1 day after said second increase.

27. A birth control method comprising the steps of:

(a) predicting the fertile period of a female mammal by monitoring the variation in concentration of at least one volatile sulfur compound of the mouth air of said mammal for said volatile sulfur compound by beginning said monitoring at the cessation of menses, said variation preceding by approximately 5 to 7 days the occurrence of ovulation of said mammal and the time of ovulation of said mammal;

(b) providing an indicator means for qualitatively and quantitatively responding to variations in the concentration of said volatile sulfur compound in said mouth air, wherein a first response of said indicator means indicating an increase in said volatile sulfur compound concentration predicts the onset of the fertile period by from between 2 and 4 days and wherein a second response to said indicator means indicating an increase in said volatile sulfur compound concentration and occurring at least 4 days after said first response indicates ovulation; and (c) causing said mammal to avoid exposure to fertilization beginning no more than 2 days after said first increase and ending at least 2 days after said second increase.

* * * * *